United States Patent [19]
Santini

[11] Patent Number: 5,352,698
[45] Date of Patent: Oct. 4, 1994

[54] METHODS OF TREATMENT FOR PATIENTS SUFFERING FROM RILEY-DAY DISEASE

[76] Inventor: Maurizio Santini, Via Vanvitelli, 19, 20129 - Milan, Italy

[21] Appl. No.: 945,665

[22] Filed: Sep. 16, 1992

[30] Foreign Application Priority Data

Sep. 17, 1991 [IT] Italy .............................. MI91A-02444

[51] Int. Cl.$^5$ ...................... A61K 31/27; A61K 31/22
[52] U.S. Cl. ..................................... 514/478; 514/546
[58] Field of Search ........................ 514/478, 479, 546

[56] References Cited

U.S. PATENT DOCUMENTS

| | | | |
|---|---|---|---|
| 4,271,143 | 6/1981 | Schoenwald et al. | 514/478 |
| 4,857,534 | 8/1989 | Croom, Jr. et al. | 514/478 |
| 5,084,281 | 1/1992 | Dillon | 514/478 |

*Primary Examiner*—Raymond I. Henley, III
*Attorney, Agent, or Firm*—Bucknam and Archer

[57] ABSTRACT

A pharmaceutical product is disclosed which interferes with pathologies of human sensitivity and of the motor system. This product comprises parasympathomimetic drugs, in particular carbachol, methacholine or bethanechol and is useful for treating patients suffering from Riley-Day disease.

4 Claims, No Drawings

METHODS OF TREATMENT FOR PATIENTS SUFFERING FROM RILEY-DAY DISEASE

BACKGROUND OF THE INVENTION

The present invention relates to a pharmaceutical product comprising a parasympathomimetic drug having therapeutic properties on the pathology of human sensitivity and of the motor system in general.

Parasympathomimetic drugs are already known, the effect of which is similar to that which is obtained by stimulating the parasympathetic postganglionic fibres.

The fact is also known that these drugs are at present rarely used since their action throughout the sensory periphery is little known.

In this connection it should be pointed out that the applicant has elaborated a theory about a "sympathetic-sensory coupling" (SSC), by postulating ubiquitous sympathetic inhibitions throughout the sensory periphery.

Considering the well-known sympathetic-parasympathetic parallelism on smooth muscle, glands and myocardium, the same applicant has experimentally exploited the parasympathetic denervation supersensitivity of familial dysautonomia (Riley-Day disease) and he has reversed with parasympathomimetic drugs the skin and corneal analgesia, the ageusia, anosmia and proprioceptive and vestibular areflexia of this disease, thus experimentally showing for the first time the existence of excitatory "parasympathetic-sensory couplings" (PSC).

Moreover, he has integrated this discovery the general theory of the "sympathetic and parasympathetic sensory coupling" (SPSC), and into the essential distinction between the following peripheries:

1) normechanoceptive, nornociceptive, norproprioceptive and
2) dysmechanoceptive, dysnociceptive, dysproprioceptive.

This theory postulates the existence of normal normechanoceptors, nornociceptors and norproprioceptors which are excited by the parasympathetic system and inhibited by the sympathetic one; and that, "in the case of a parasympathetic denervation, parasympathetic drugs can replace the excitatory action of the parasympathetic system thereon.

Vice versa, in the case of a biochemical alteration of the axoplasmic flow of the primary sensory neurons, due to a central or peripheral cause, these neurons may display membrane dysmetabolic characteristics which transform normechanoceptors into dysmechanoceptors, nornociceptors into dysnociceptors, and norproprioceptors into dysproprioceptors.

On these dysmechanoceptors, dysnociceptors and dysproprioceptors, the parasympathetic nervous system reverses its action, from being excitatory on to the normechanoceptors, nornociceptors and norproprioceptors, into being an inhibitory one.

However, the parasympathetic action becomes very small or absent, because of the prevalence of an excitatory action of the sympathetic nervous system on dysmechanoceptors, dysnociceptors and dysproprioceptors.

The same applicant has pointed out a broad applicability of this theoretical innovation particularly in the medical and neurological field.

Within this general heuristic context, the applicant has exploited the denervation-supersensitivity of parasympathetic denervation on sensory receptors, and he has elevated it to a conspicuous indication of the general principle of ubiquitous "parasympathetic sensory couplings", which up to now have been almost unknown in the neurological field, because of the dogmatic and exclusive ideology of the unidirectionality of "sense" (from-periphery-to-center) and of motion (from-centre-to-periphery).

Substantially, by means of classical and modern aesthesiometric tests, such as the Stockholm thermotest (which measures the pain on the skin due to warm and cold), the "Zottmeter" (a new quick skin algometer) and by means of other aesthesiometric devices, such as that of Cochet-Bonnet and the "Leibnizmeter" for corneal aesthesia, the non Frey bristles for skin and mucous aesthesia, and the geusimeter for gustatory aesthesia, the applicant has experimentally verified the above mentioned SPSC theory, in several clinical situations of hypoaesthesia and/or of cutaneous and corneal nornociceptive and normechanoceptive anaesthesia and of the oral mucosa.

In addition to more or less relatively rare neurological situations, but of great theoretical interest for verifying the SPSC theory, such as the above mentioned Riley-Day disease, ectodermal dysplasia, corneal hypoaesthesia due to acoustic neurinoma or to invasive pathology of the pontocerebellar angle, neuropathy and leprosy, the same applicant has moreover reversed, by means of parasympathomimetic drugs (in particular with carbachol and/or methacholine and/or ehtyletherbeta methylcholine cloride and/or bethanechol, normechanoceptive and nornociceptive hypoaesthesias, in 315 out of 337 cases of diabetic neuropathy.

Moreover, the same applicant has reversed, by means of the above mentioned drugs, skin normechanoceptive and nornociceptive hypoaesthesias and anaesthesias in 36 senile subjects both male and female having an average age of 74.3 years), not affected by relevant pathologies. It was found that also their reaction times were improved.

The duration of the effect of a single dose was found to vary from 26 hours to 15 days depending the cases.

That same effect, in particular, could be restored by means of a new administration.

The applicant has moreover experimentally verified the SPSC theory also in the case of 31 paraplegic patients and, by means of parasympathomimetic drugs, has reversed skin nornociceptive and normechanoceptive anaesthesias (also in three cases on the penis gland, with an orgastic restitution). The sensory receptors of such anesthetic skin were obviously still transynaptically connected with the sensory cortex, but removed from the facilitatory parasympathetic tonic action—which is a mandatory condition for sensory transduction—because of the spinal interruption of descending excitatory pathways on the parasympathetic preganglionic neurons.

Seven of these paraplegic patients recovered variable degrees of voluntary movement of the toes dorsi-flexion of the foot, abduction and adduction, as well as extension and flexion of the lower limbs.

By means of the above-mentioned experimental verifications, the applicant has been able to consider further, and to exploit, the possible presence of parasympathetic fibers near the sympathetic ones in the muscle spindle, after parasympathomimetic drugs had reversed the proprioceptive areflexia of the Riley-Day syndrome.

Thus, the applicant has been able to verify the motor aspect of the SPSC theory, by restoring 1) several degrees of motor capability, sometimes even a near complete restitution ad integrum of the whole limb of the hand, foot, fingers or toes, starting from an absolute inability of movement;

2) non-assisted deambulation in patients who could walk but with means of support or who were not able to walk at all.

This has been obtained in 147 out of 172 hemiplegic patients by using the above-mentioned parasympathomimetic drugs, and, more specifically:

in 3 out of 5 acute hemiplegic patients (up to 2 days from the cerebral damage);

in 11 out of 15 subacute hemiplegic patients (from 22 days to 6 months);

in 120 out of 137 stabilized chronic hemiplegic patients (from 7 months to 8.4 years);

in 13 out of 15 hemiplegic patients with a posthemiplegic shoulder-hand syndrome, in all of whom the dysnociceptive pain was also removed.

In 81 out of 102 of these hemiplegic patients, tested ad hoc, in particular, cutaneous normechanoceptive and nornociceptive hypoaesthesias or anaesthesias were reversed by the above-mentioned parasympatnomimetic drugs.

By using the above-mentioned parasympathomimetic drugs, moreover, normechanoceptive and nornociceptive skin anaesthesias or hypoaesthesias were also reversed in 25 out of 26 cases of multiple sclerosis, by also restituting to the treated patients the two above-mentioned patterns of motor-reinitiation obtained in the hemiplegic patients.

The applicant has found in three patients affected by a Strumpell-Lorraine syndrome and who had been treated with the above-mentioned parasympathomimetic drugs, a very good recovery of deambulation which was reversed from an assisted status to a nonassisted one, as well as an improvement of their tactile and pain sensitivities.

The applicant has moreover treated three patients affected by amyotrophic lateral sclerosis by the above-mentioned parasympathomimetic drugs. Two of the patients were affected in their lower limbs and were improved, passing from an assisted deambulation to a non-assisted one.

One patient affected in his upper limbs also recovered a reasonable manual work activity. Also the tactile and pain sensitivities of these patients were improved.

An improvement of movement, sometimes with a restoration of non-assisted deambulation, has been obtained by treating with parasympathomimetic drugs patients affected by the Eaton-Lambert syndrome (5 cases), patients affected by myasthenia gravis (9 cases) and patients affected by muscular dystrophy particular the Duchenne disease, 11 cases). Also the tactile and pain sensitivities of these patients were greatly improved.

The applicant has moreover found a parasympathomimetic reduction, sometimes up to a disappearance of muscle spasticity, even resistant to the antispastic treatment, in patients affected by paraplegia, hemiplegia and multiple sclerosis.

These parasympathomimetic drugs were moreover advantageously used to inhibit pain pathology resulting from dysnociceptors and dysmechanoceptors, due to a biochemical lesion of the axoplasmic flow in nociceptive and mechanoceptive neurons, due either to a peripheral or a central cause as in the above-mentioned) post-hemiplegic shoulder-hand syndrome and in the dysnociceptive and dysmechanoceptive dysaesthesias resulting from a central lesion in general, as well as in paraplegic patients and in those affected by multiple sclerosis.

In this connection it should be pointed out that the applicant has experimentally verified his SPSC and centroperipherorecursive theory in pains from chronic dysnociceptors of a peripheral cause, by greatly reducing, and also zeroing, by means of the above-mentioned parasympathomimetic drugs, pain also of the drug-resistant type in:

25 out of 28 patients affected by chronic rheumatoid arthritis;

18 out of 19 patients affected by chronic arthrosis;

22 out of 25 patients affected by chronic coxarthrosis and chronic relapsing sciatica.

Moreover, after using the above-mentioned parasympathomimetic drugs, aesthesiometric tests were carried out which reversed cutaneous hypoesthesias-anaesthesias of 32 patients affected by arterial hypertension whose therapies had been suspended.

The applicant has detected significant reductions of their systolic and diastolic blood pressure down to normal values.

These reductions in blood pressure values could be repeated in a causal relation so as to guarantee a control of blood pressure without the use of any other antihypertensive drug, for the whole period of treatment, up to four weeks of observation.

Likewise, during aesthesiometric tests done to cause a reversal, by the above-mentioned parasympathomimetic drugs, of cutaneous hypoesthesias and anaesthesias in 15 patients affected by an arteriopathy of the upper limbs (Raynaud disease and syndrome, and sclerodermia in particular) and of the lower limbs, the applicant found, in addition to the aesthesiometric reversal of hypoaesthesia-anaesthesia improvement of the vasculopathic status, as detected plethismographically, which was accompanied by a reduction and also by a disappearance of the pain of claudicatio intermittents.

Finally, after tests reversing normechanoceptive and nornociceptive hypoesthesias-anaesthesias by using the above-mentioned parasympathomimetic drugs, in 21 patients affected by Down disease, 9 patients affected by Alzheimer disease, and 11 patients affected by autism, it was possible to improve the reaction times of all these patients.

These results were replicated in a causal relation, for the whole treatment time, up to four weeks.

In 12 out of 21 patients affected by the Down disease, the applicant found a drastic improvement muscle tone and movement.

From the above disclosure there results that the applicant's claim about the use of parasympathomimetic drugs in general, in particular carbachol and/or methacholine and/or ethyl ether beta-methyl choline chloride and/or bethanechol, in the medical and neurogical clinical fields is broadly justified.

With respect to the optimum doses of parasympathomimetic drugs which have been found to be active in the diseases disclosed above, the following daily doses are indicated:

1) CARBACHOL: 0.3–9 mg supra cutem and/or 0.25–0.75) mg i.m. pro die;

2) METHACHOLINE: 0.3-9 mg supra cutem and-/or 0.15-0.75 mg i.m. pro die;

3) ETHYL ETHER BETA-METHYLCHOLINE CHLORIDE: 0.3-9 mg supra cutem pro die;

4) BETHANECHOL: 0.3-15 mg supra cutem and/or 5-15 mg i.m. pro die.

Within these dose ranges no side effect was ever found, either topically on the skin, or systemically.

It should be pointed out that while the best pharmacological an therapeutical results have been obtained by using the four above-mentioned chemical compounds, it has been experimentally found that the whole spectrum of parasympathomimetic drugs exhibited similar therapeutical characteristics.

From the above it should be apparent that the invention is intended to also encompass, with respect to the above-disclosed therapeutical uses and indications, all the classes of the parasympathomimetic compounds.

We claim:

1. A method of treatment of a human subject affected by cutaneous and corneal analgesia, ageusia, anosmia and proprioceptive and vestibular areflexia of the Riley-Day disease which consists of administering supra cutem or i.m. to said human subject a composition containing 0.3-9 mgs of carbachol per dose for supra cutem or 0.25-0.75 mgs or carbachol per dose for i.m. administration.

2. A method of treatment of a human subject affected by cutaneous and corneal analgesia, ageusia, anosmia and proprioceptive and vestibular areflexia of the Riley-Day disease which consists of administering supra cutem or i.m. to said human subject a composition containing 0.3-9 mgs of methacholine per dose for supra cutem of 0.25-0.75 mgs. of methacholine per dose for i.m. administration.

3. A method of treatment of a human subject affected by cutaneous and corneal analgesia, ageusia, anosmia and proprioceptive and vestibular areflexia of the Riley-Day disease which consists of administering to said human subject a composition containing 0.3-9 mgs of the ethyl ether of beta methylcholine chloride per dose for supra cutem administration.

4. A method of treatment of a human subject affected by cutaneous and corneal analgesia, ageusia, anosmia and proprioceptive and vestibular areflexia of the Riley-Day disease which consists of administering supra cutem or i.m. to said human subject a composition containing 0.3-15 mgs of bethanechol per dose for supra cutem of 5-15 mgs of bethanechol per dose for i.m. administration.

* * * * *